United States Patent
Blit et al.

(10) Patent No.: US 9,026,192 B2
(45) Date of Patent: May 5, 2015

(54) DEVICE AND METHOD FOR IN VIVO IMAGING

(75) Inventors: Shmuel Blit, Rehovot (IL); Elisha Rabinovitz, Haifa (IL)

(73) Assignee: Given Imaging Ltd, Yoqneam (IL)

( * ) Notice: Subject to any disclaimer, the term of this patent is extended or adjusted under 35 U.S.C. 154(b) by 1183 days.

(21) Appl. No.: 12/954,501

(22) Filed: Nov. 24, 2010

(65) Prior Publication Data

US 2011/0125031 A1    May 26, 2011

Related U.S. Application Data (60) Provisional application No. 61/263,933, filed on Nov. 24, 2009.

(51) Int. Cl.
- *A61B 5/05* (2006.01)
- *A61B 5/07* (2006.01)
- *A61B 5/00* (2006.01)

(52) U.S. Cl.
CPC ............ *A61B 5/073* (2013.01); *A61B 5/0062* (2013.01); *A61B 5/0071* (2013.01); *A61B 5/0075* (2013.01); *A61B 5/0084* (2013.01)

(58) Field of Classification Search
CPC ... A61B 5/0062; A61B 5/0084; A61B 5/0071
USPC .......................................... 600/407, 473–475
See application file for complete search history.

(56) References Cited

U.S. PATENT DOCUMENTS

| | | | |
|---|---|---|---|
| 5,604,531 A | 2/1997 | Iddan et al. | |
| 7,460,896 B2 | 12/2008 | Iddan | |
| 2001/0035902 A1 | 11/2001 | Iddan et al. | |
| 2002/0173718 A1 | 11/2002 | Frisch et al. | |
| 2006/0036166 A1 | 2/2006 | Horn | |
| 2008/0027329 A1 | 1/2008 | Glukhovsky | |
| 2008/0119740 A1 | 5/2008 | Iddan | |
| 2010/0198081 A1* | 8/2010 | Hanlin et al. | 600/478 |

* cited by examiner

*Primary Examiner* — Unsu Jung
*Assistant Examiner* — Joel Lamprecht
(74) *Attorney, Agent, or Firm* — Pearl Cohen Zedek Latzer Baratz LLP (57) ABSTRACT

Devices and methods for optically scanning an in-vivo lumen, and for determining contact between an in-vivo device and an in-vivo lumen wall. The device may include an elongated housing having a cylindrical portion. At least one illuminating body may provide illumination at the circumference of the cylindrical portion, and at least one light sensor may sense light that penetrated and was scattered from the tissue of the in vivo lumen. The device may include a barrier for preventing direct illumination from the illuminating body from reaching the light sensor and for decreasing the amount of direct light reflection from the outer surface of the in vivo lumen onto the light sensor.

16 Claims, 6 Drawing Sheets

DEVICE AND METHOD FOR IN VIVO IMAGING

CROSS-REFERENCE TO RELATED APPLICATIONS

This Application claims the benefit of United States Provisional Application Ser. No. 61/263,933, filed Nov. 24, 2009, which is hereby incorporated by reference in its entirety.

FIELD OF THE INVENTION

The present invention relates to an in-vivo device and method for imaging an in-vivo lumen. More specifically, the present invention relates to an autonomous in vivo sensing and/or imaging device and method for imaging scattered light and for detecting pathologies of in-vivo lumens, e.g., of the gastrointestinal (GI) tract wall, using scattered light analysis and spectral analysis methods.

BACKGROUND OF THE INVENTION

Known devices may be efficient in providing in-vivo sensing, such as imaging or pH sensing. Autonomous in-vivo sensing devices, such as swallowable or ingestible capsules or other devices, may move through a body lumen, sensing as they move along. An autonomous in-vivo sensing device such as an imaging device may include, for example, an imager for obtaining images from inside a body cavity or lumen, such as the GI tract, while the in-vivo imaging device passes through the GI lumen. The imager may, for example, be associated with an optical system, and optionally a transmitter and an antenna. Some of these devices use a wireless connection to transmit image data. Other devices, systems and methods for in-vivo sensing of passages or cavities within a body, and for sensing and gathering information (e.g., image information, pH information, temperature information, electrical impedance information, pressure information, etc.), are known in the art.

Viewing and detecting pathologies in the GI tract, such as tumors, lesions, ulcers, polyps and the like may be complicated due to different parameters such as the fact that the item or pathology sought to be viewed may have very similar color and texture as the color and texture of its background tissue or by the fact that a pathology may be too small to visualize using standard in-vivo imaging methods.

Different methods exist for enhancing detection of pathologies in-vivo. Such methods may include the use of spectral imaging dynamic light scattaring and different image processing techniques, with or without the use of external markers that distinguish the pathologies from the surrounding tissues.

Scattering is a basic physical phenomenon by which the propagation of light through a turbid biologic tissue can be used as the basis for quantitative non-invasive measurements. The interaction of light with tissue is composed of multiple internal refractions and redirections of the incident light emanating from the collisions of light photons with molecules, particles, boundaries and inhomogeneities of the tissue, as and such this interaction is structure associated. It is well known that lesions and pathologies change the structure and composition of a healthy tissue, and early detection of such pathologies may enable faster recovery of the tissue. The changes in scattering caused by the tissue's inner structure and composition can be quantitatively measured.

Currently, commercial capsule endoscopes typically include one or more imagers made of two-dimensional array of pixels (e.g., 256×256 pixels), such that in every exposure a two-dimensional image is captured and transmitted. Usually, the imager looks in a direction parallel to the longitudinal axis of the capsule endoscope. A dome shaped optical window is used to ensure that the image is acquired when the illumination source of the capsule endoscope is at a distance from the tissue. When the illumination source is at a distance from the tissue, light is reflected predominantly off the outer surface of the tissue, such that the image acquired is mainly of the outer surface of the lumen wall tissue, while the inner layers of the tissue is masked.

A device and method for collecting and measuring oximetry data in a body lumen are described in U.S. Pat. No. 7,460,896 entitled IN-VIVO DEVICE AND METHOD FOR COLLECTING OXIMETRY DATA, which is assigned to the common assignee of the present invention. According to embodiments described in U.S. Pat. No. 7,460,896, a red or infra-red illumination source and an oximetry data detector are located in close proximity to one another, while both being in close proximity to the lumen wall tissue, such that most of the light emitted from the tissue is red light that was diffused from inner layers of the tissue, indicating on oxygenation of hemoglobin in the blood.

A device and method for collecting and separating light reflected from a body lumen are described in U.S. Patent Application Publication No. 2008/0119740 entitled DEVICE, SYSTEM, AND METHOD FOR OPTICAL IN-VIVO ANALYSIS, which is assigned to the common assignee of the present invention. According to embodiments described in U.S. Patent Application Publication No. 2008/0119740, a panoramic mirror reflects light that is reflected from the body lumen, onto a separator (e.g., prism or grating), which separates the reflected light into separate color lights. The separate color lights are then reflected onto an analyzer which analyzes them.

There is a need for a device and method for determining changes in tissue texture and spectral content based on changes in scattered light from more than one area of the tissue. There is further a need for a device of low manufacturing cost.

SUMMARY OF THE INVENTION

Embodiments of the invention provide a device that may scan a lumen wall in-vivo, typically illuminating in flashes or continuously, and may provide a high resolution image of the wall, thus providing an energy efficient and improved device and method for detecting pathologies on or beneath the surface of the lumen wall.

According to embodiments of the invention, at least in some regions of the lumen, the in-vivo device provided is substantially in contact with or is in close proximity to the lumen wall, such that light penetrates the tissue and surface reflections are avoided. According to some embodiments, internal layers of the tissue may be analyzed, thereby providing information that cannot be obtained in-vivo by the prior art imaging methods.

According to some embodiments, the in-vivo device may comprise an illumination source in proximity to a pixel size sensor, both of which may be substantially in contact with or in close proximity to the surface of the lumen tissue, thereby scanning the inner layers of the tissue for changes in its structure. In order to avoid specular reflections from the surface of the lumen wall tissue, the in-vivo device may be substantially in contact with the lumen wall tissue, specifically at the small bowel region. The device may reach direct contact with the lumen wall through various methods. In some embodiments, the device may be a tip of an endoscope, a guided capsule endoscope or a passively moving capsule having a diameter such that the lumen wall (of either the small or large intestine), when shrinking due to a peristaltic wave or when collapsed, may surround it from substantially all sides of the device's circumference. For example, the diameter of the device may be within the range of 10-16 mm, yet the device may have other diameters.

Furthermore, according to some embodiments, the device may comprise a barrier placed between the illumination sources and the light sensors so as to block almost any reflection reflected off the surface of the lumen wall tissue from masking the relatively faint light that emits from inside the tissue. In some embodiments, when the device is substantially in contact with the lumen wall or with the surface of the tissue, the received signal may contain scattering information and sub-surface spectral information, thereby providing information on tissue texture, which may provide an indicate of pathologies present in the tissue. In other embodiments, the device comprising a pixel sized sensor may further comprise illumination sources illuminating at various wavelengths, thereby providing spectral analysis of the tissue, i.e., the light reflected, transmitted and scattered from the tissue at the different wavelengths may give more information relating to tissue characteristics than light reflected and transmitted at one wavelength. According to some embodiments, the illumination source may be pixel sized as is the light sensor, so as to be able to couple between the illumination source and its light sensor, whereas each pair of illumination source and light sensor may be designed to collect information at a different wavelength.

According to embodiments of the present invention, a plurality of (pixel sized) illumination sources coupled with a plurality of pixel sized light sensors located on the periphery of the in-vivo device, e.g., radially, may provide a radial scan of the lumen wall. A plurality of light sensors may acquire a spatial distribution and spectral distribution of scattering from the inner layers of the lumen wall tissue.

In some embodiments, the pixel sized illumination sources coupled to pixel sized sensors may be part of a device comprising an image sensor positioned either at one end or at both ends of the elongated device. The imager or imagers may be positioned perpendicularly to the direction of movement of the device along the lumen, thus providing images of the surface of the lumen wall as well as images of the sub-surface radial lumen wall.

According to embodiments of the invention, the device comprising the pixel sized illumination sources coupled to the pixel sized sensors may be an autonomous swallowable capsule. According to other embodiments, the pixel sized illumination sources coupled to pixel sized light sensors may be part of a maneuverable device, e.g., as ingestible guided capsule endoscope, which may comprise an imager or video camera located perpendicular to the longitudinal axis of the capsule. In some embodiments, the imager may be located on one end of the capsule's longitudinal axis; while the pixel sized illumination sources coupled to pixel sized light sensors may be located on the opposite end of the capsule's longitudinal axis. Unless maneuvered to a different direction, such a guided capsule may provide images of the GI tract tunnel, while the capsule moves forward at the same motion as the peristalsis motion of the GI tract. However, such a capsule may be guided to observe a lesion, which may be located onto the tissue wall, i.e., parallel to the longitudinal axis of the device. The guided capsule may then be rotated in 90 degrees relative to the pixel sized sources and sensors, such that the pixel sized sources and sensors may be in contact with the lesion. The guided capsule may also be rotated in 90 degrees relative to the imager's end, thus enabling image acquisition of the lesion. According to other embodiments, the device may be part of an endoscope, e.g., the tip of an endoscope.

BRIEF DESCRIPTION OF THE DRAWINGS

The present invention will be understood and appreciated more fully from the following detailed description taken in conjunction with the drawings in which.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Figure 1:
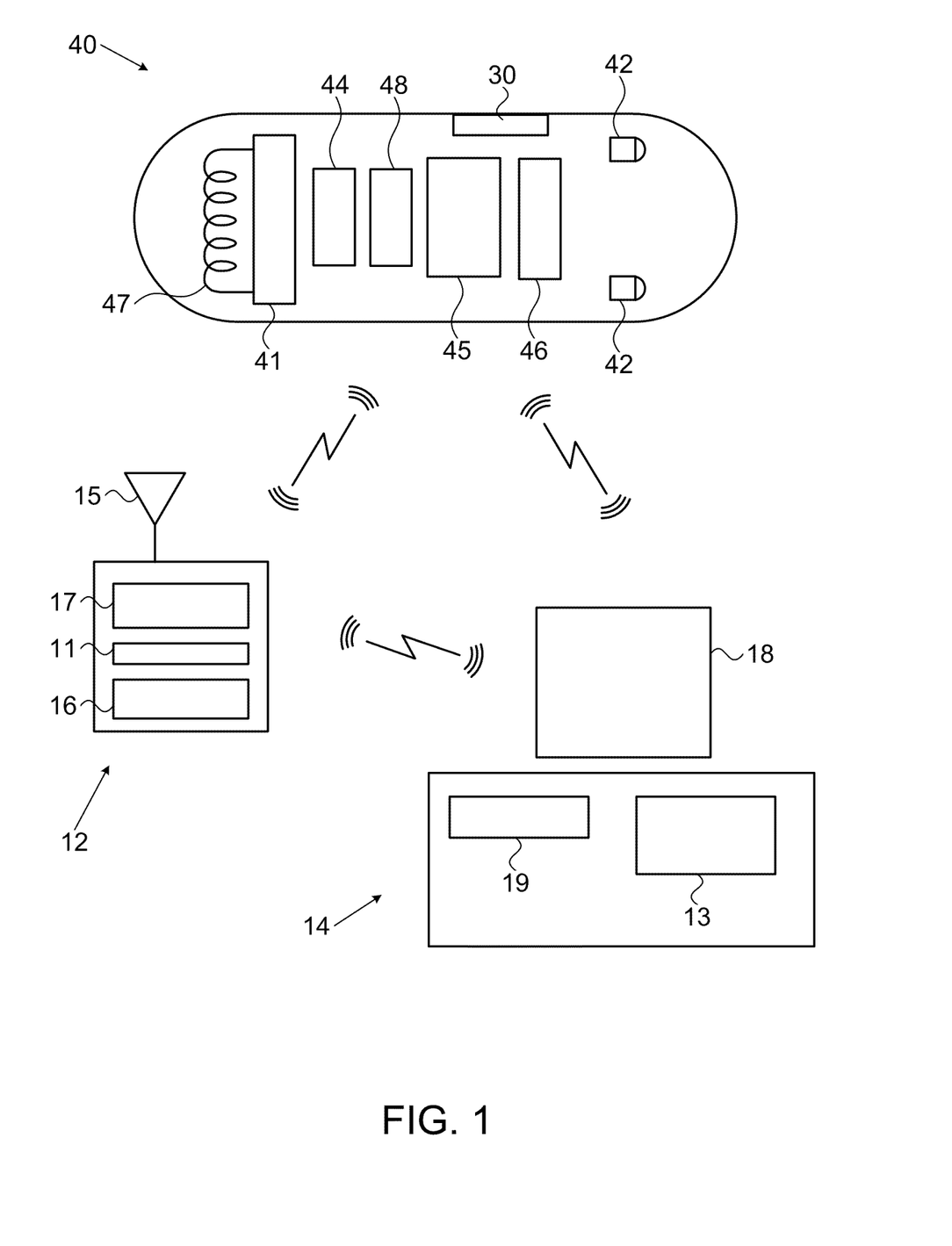
FIG. 1 is a schematic illustration of a device and system according to an embodiment of the invention.

Reference is made to FIG. 1, which shows a schematic diagram of an in-vivo imaging system according to an embodiment of the present invention. Typically, the in-vivo imaging system may include an in-vivo imaging device 40, an external receiving device and/or recording device 12, e.g., data receiver, and a workstation 14. The in-vivo imaging device 40 may have an imager 46 for capturing image frames or a stream of image frames, an illumination source 42 for illuminating the body lumen, a power source 45 for powering device 40, a processor 44 for processing data and commands to and from device 40, a transmitter 41 with antenna 47 for transmitting image and possibly other data to an external receiver 12, and a nevigation device 48. In some embodiments of the present invention, in-vivo device 40 may include one or more sensors 30, in addition to or in replacement of imager 46, for example, temperature sensors, pH sensors, pressure sensors, blood sensors, tracking sensors, etc. Imager 46 may be a CCD or CMOS imager, or may be another solid state imaging device or other imaging device According to some embodiments, one or more dedicated, typically small (for example, pixel sized) light sensors may be included in the device 40, as will be further described below Illumination source 42 may include one or more LEDs or other illumination sources. According to some embodiments, one or more dedicated, typically pinpoint light sources may be included in the device 40, in addition to illumination source 42, as will be further described below.

In some embodiments of the present invention, device 40 may be an autonomous device, a capsule, or a swallowable capsule. In other embodiments of the present invention, device 40 may be a swallowable capsule that may be navigated. In yet other embodiments, device 40 may not be autonomous, for example, device 40 may be an endoscope or other in-vivo device.

Embodiments of the invention need not include imager 46 and/or illumination source 42 and may include only the dedicated light sources and dedicated light sensors.

The in-vivo imaging device 40 may typically, according to an embodiment of the present invention, transmit information (e.g., images, spectral data or other data) to an external receiver 12, which may possibly be close to or worn on a subject. Typically, the receiver 12 may include an antenna or antenna array 15 and a data receiver storage unit 16. Typically antenna array 15 may pick up signals transmitted by device 40 or the transmitter 41 and antenna 47 of device 40. The external receiver 12 may include one or more processors 17 for processing image data or other data.

Receiver 12 may include a tracking unit 11, for tracking the location of an autonomous in-vivo imaging device 40 over time. For example, tracking unit 11 may track the location of device 40 in three dimensional space over time and/or may track the distance, for example the distance over time that device 40 traveled through the GI tract or through a specific organ in the GI tract over time. Tracking unit 11 may be similar to various embodiments described, for example, in U.S. Patent Application Publication No. 2002/0173718 published on Nov. 21, 2002 and U.S. patent application Ser. No. 10/879,053 filed on Jun. 30, 2004 both of which are assigned to the common assignee of the present application and incorporated herein by reference in their entirety. Other known tracking units or methods of tracking a device may be used. In other embodiments, the tracking unit 11 or part of its functionality may be included in device 40. The receiver 12 may take on other suitable configurations and may not include an antenna or antenna array. In one embodiment of the present invention, the receiver 12 may include, for example, an LCD display for displaying image data or other data, e.g., tracking data. In other embodiments, receiver 12 may be electrically connected, e.g., via wire, blue tooth or wireless connection, to a display unit, e.g., display unit 18 or workstation 14, in order to display data transmitted by in-vivo device 40 and/or processed by processing unit 17, 44, or workstation 14.

In one embodiment of the present invention, the receiver 12 may, for example, receive and store data from imaging device 40, e.g., an image data stream captured and/or processed by processor 17, and later transfer the received data to a workstation 14, such as a personal computer, laptop or other portable or stationary computing devices, where the data may be further analyzed, stored and/or displayed to a user, e.g., a health professional. Typically, workstation 14 may include processing unit 13, data processor storage unit 19, a disk drive, input-output devices, and display unit 18, e.g., a monitor, although alternate configurations are possible. Processing unit 13 may typically, as part of its functionality, act as a controller in controlling the display of data, for example, image data or other data. Display unit 18 may typically be a conventional video display, but may, in addition, be any other device capable of providing image or other data. Instructions or software for carrying out a method according to an embodiment of the invention may be included as part of workstation 14, for example stored in memory 19.

In other embodiments, each of the various components need not be required; for example, the in-vivo device 40 may transmit or otherwise transfer (e.g., by wire) data marking image frames that may be candidates for pathology identification directly to a viewing device or workstation 14. In one embodiment of the present invention, device 40 may only transmit selected image frames.

In-vivo imaging systems suitable for use with embodiments of the present invention may be similar to various embodiments described, for example in U.S. Pat. No. 5,604,531, entitled "In-Vivo Video Camera System", assigned to the common assignee of the present application and incorporated herein by reference in its entirety, and/or U.S. Patent Application Publication No. 20010035902 published on Nov. 1, 2001 and entitled "Device and System for In-Vivo Imaging", also assigned to the common assignee of the present application and incorporated herein by reference in its entirety.

Other in-vivo systems, having other configurations, may be used. Of course, devices, systems, structures, functionalities and methods as described herein may have other configurations, sets of components, processes, etc.

Figure 2A:
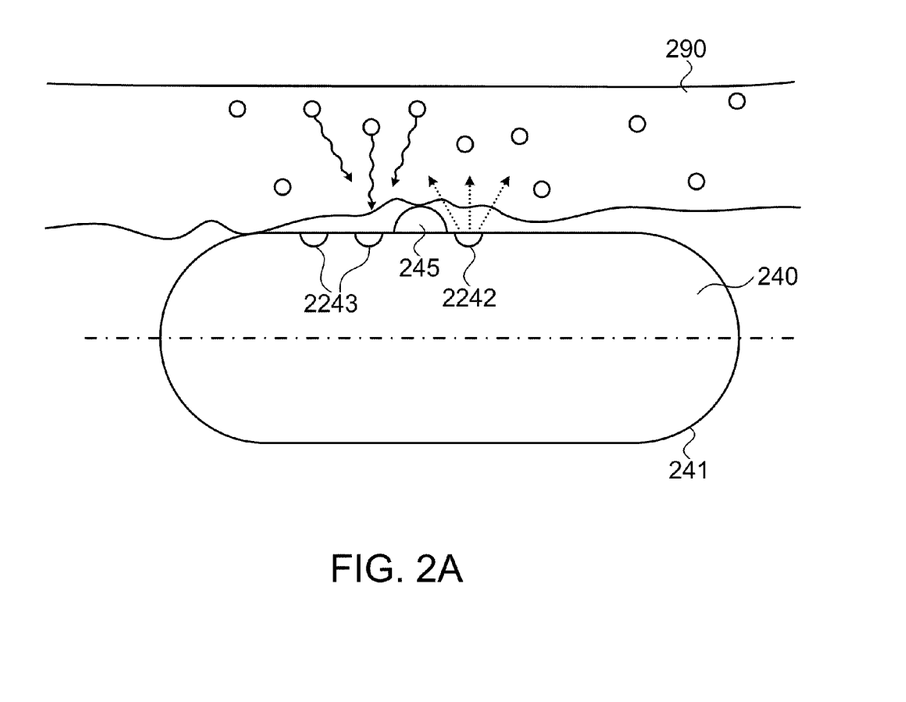
FIGS. 2A-2B are schematic illustrations of an imaging device and operation thereof, according to embodiments of the invention.
Figure 2B:
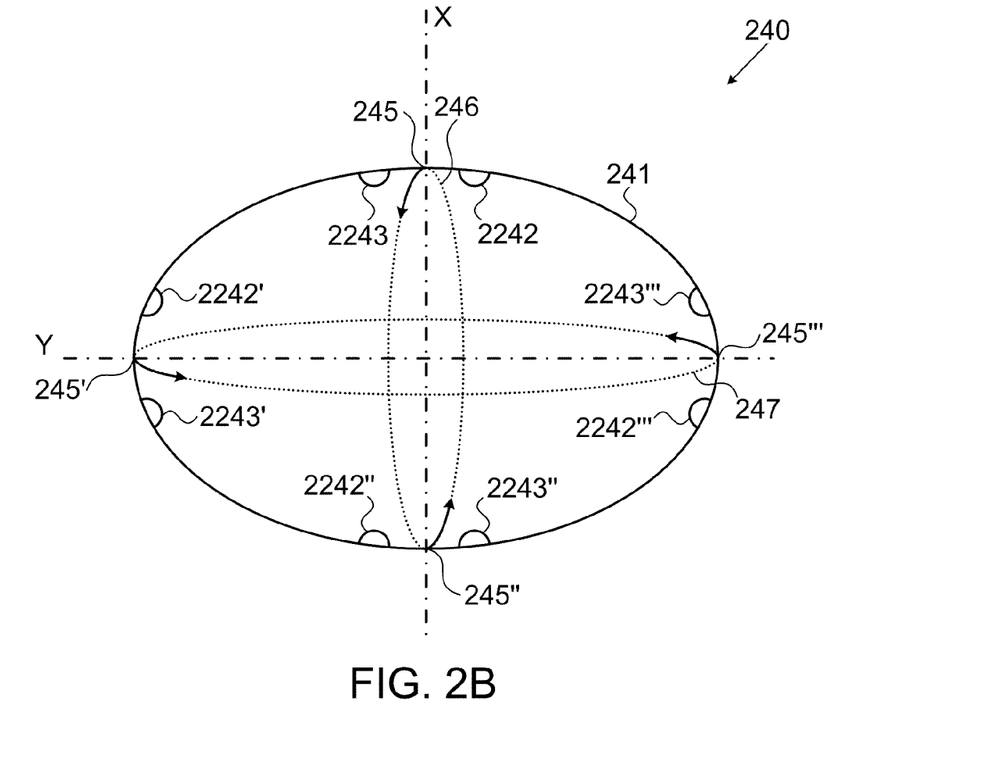

Reference is now made to FIGS. 2A-2B, which schematically illustrate in vivo imaging devices according to embodiments of the invention. According to one embodiment, the device 240 in either of FIG. 2A or 2B may be similar to and may include components similar to device 40 described in FIG. 1.

According to one embodiment, device 240 may be a capsule shaped device or another shaped device which may facilitate swallowing of the device. Device 240 may include a housing 241 which encapsulates the device components. The housing 241 may include one or more optical openings 2242 through which dedicated illuminating body 242 (shown in FIG. 3) may illuminate the environment outside device 240, for example the GI tract wall tissue 290. Housing 241 may also include one or more optical openings 2243 behind which dedicated lights sensor(s) 243 (shown in FIG. 3) may be placed so that it/they may receive light scattered through the GI tract tissue 290.

According to one embodiment, a barrier 245 is positioned on the housing 241 such to avoid direct light emanating from illuminating body 242 from reaching light sensor 243. Typically, during the passage of the device through certain lumens of the GI tract, such as the small bowel or the colon during contraction, the barrier is substantially in contact with the lumen wall or tissue surface. Therefore, barrier 245 may further prevent light reflected from the outer surface of the lumen wall tissue from directly reflecting onto light sensors 243 or may decrease the amount of light directly reflecting to it and thus prevent masking of the faint light that emits from the inner layers of the tissue.

According to some embodiments, the barrier 245 may protrude from the surface of the cylindrical portion of the elongated housing of device 240. According to some embodiments, the barrier 245 may be a ring circling the housing 241. According to some embodiments, the barrier 245 may be integral to housing 241. Other means for decreasing the amount of direct illumination and/or direct surface reflection onto light sensor 243 are possible; for example, according to some embodiments the illuminating body 242 and/or the light sensor 243 may be positioned in niches or recessed parts of the housing, thus being partitioned from one another so as not to allow direct light from illuminating body 242 reach light sensor 243 and decrease the amount of direct surface reflection onto it.

Upon insertion of the device 240 into a patient's GI tract (for example, by swallowing or by otherwise placing the device in the patient's GI tract), illuminating body 242 may illuminate the GI tract wall tissue 290, typically in a non continuous manner, for example at a rate of 10 flashes per second. Other rates and/or lighting periods may be used. In some embodiments, substantially continuous illumination may be used. Sensing of light remitted and/or scattered from the GI tract, which is typically light that penetrates the lumen wall tissue and is then emitted or scattered from the lumen wall tissue, may also be in a non continuous manner to obtain overlapping signals or images and furthermore to effectively manage device 240 energy supply. According to some embodiments, light sensor(s) 243 may acquire data of light remitted from the GI tract wall at a rate of 2-100 measurements per second. Other rates or sensing periods may be used.

Typically, light which penetrates the lumen wall tissue in the GI tract and is then remitted and/or scattered from the wall tissue contains relevant data on characteristics of the GI tract's wall tissue and of pathologies, if any, therein. Therefore, according to some embodiments, when device 240 passes passively through the GI tract, the housing of the device 240 is shaped as an elongated body (e.g., a cylinder, an ellipsoid or other elongated shapes) having a dome-shaped or convex end at each side of its longitudinal axis. In these embodiments, the illumination body 242 and light sensor 243 are preferably positioned on the cylindrically shaped circumference of device 240, instead of being positioned on the convex ends of device 240, where during the passive passage through lumens, such as the small bowel, there may usually be less continuous contact with lumen wall. When device 240 is substantially in contact with the lumen wall, only residual light photons from illumination body 242 may be reflected from the lumen wall's surface directly onto light sensor 243 without first penetrating the tissue, while most of the light photons reflected onto the light sensor 243 first penetrate the lumen wall tissue. In other embodiments, the cylindrical shaped device may comprise maneuvering capabilities, such that one of the two dome-shaped or convex ends may occupy a navigating camera/imager, while the illumination body 242 and light sensor 243 may be positioned on the other convex end of device 240.

According to FIG. 2B, device 240 may have a housing 241 in the shape of an ellipsoid. The larger diameter along the longitudinal axis (i.e., axis y) of the ellipsoid is located along the middle of the ellipsoid 241, where y axis and x axis intersect. The largest diameter along the y axis is denoted by reference number 246. Two areas or arcs on the circumference of housing 241, which are also located along diameter 246, may be areas/arcs 245 and 245" illustrated on opposite ends of the longitudinal y axis. Optical openings 2242 through which dedicated illuminating body 242 (shown in FIG. 3) may illuminate the lumen may be located on one side area 245, while optical openings 2243 behind which dedicated lights sensor(s) 243 (shown in FIG. 3) receive scattered light may be placed on the other side of area 245. Since diameter 246 is the largest diameter along y axis, optical openings 2242 and 2243 are inevitably located along smaller diameters along y axis, such that any area on the circumference of housing 241 along diameter 246 may act as a bather between optical openings 2242 and optical openings 2243. In such an ellipsoid, there is no need for an additional bather to be added along the circumference of the housing 241, since area/arc 245 may itself be the barrier. Accordingly, optical openings 2242" through which dedicated illuminating body 242 (FIG. 3) may illuminate the lumen may be located on one side of area/arc 245", while optical openings 2243" behind which dedicated lights sensor(s) 243 (FIG. 3) receive scattered light may be placed on the other side of area 245", while area 245" may act as a bather between the two types of optical openings 2242" and 2243".

According to another embodiment, the largest diameter along the transverse axis (i.e., axis x) of ellipsoid 241, is located in the middle of the x axis, where the x axis and the y axis intersect. The largest diameter along the transverse axis is denoted by reference number 247. Two areas or arcs on the circumference of housing 241, which are also located along diameter 247, may be areas/arcs 245' and 245''' illustrated on opposite sides of the transverse x axis. Thus, for example, in order to eliminate the need to add a barrier between the illuminating body 242 and the light sensor 243 (FIG. 3), openings 2242' through which dedicated illuminating body 242 (FIG. 3) may illuminate the lumen may be located on one side of area/arc 245', while optical openings 2243' behind which dedicated lights sensor(s) 243 (FIG. 3) receive scattered light may be placed on the other side of area 245'. In some embodiments, area 245' may act as the bather between optical openings 2242' and optical openings 2243'. Since diameter 247 is the largest diameter along x axis, optical openings 2242' and 2243' are inevitably located along smaller diameters along x axis, such that any area on the circumference of housing 241 along diameter 247 may act as a barrier between optical openings 2242' and optical openings 2243'. Accordingly, optical openings 2242''' through which dedicated illuminating body 242 (FIG. 3) may illuminate the lumen may be located on one side of area/arc 245''', while optical openings 2243''' behind which dedicated lights sensor(s) 243 (FIG. 3) receive scattered light may be placed on the other side of area 245'''. Area/arc 245''' may act as a barrier between the two types of optical openings 2242''' and 2243'''.

In addition, when device 240 touches the lumen wall and illuminating body 242 illuminates the wall, light sensor 243 may receive fluorescence photons emitted from the outer wall tissue. These fluorescence photons which are at a different wavelength than the illumination source wavelength, may contain data on tissue characteristics when emitted from the tissue itself or from markers within the tissue, or may be emitted from selectively marked pathologies if any.

Optical openings 2242 and 2243 may be pixel sized, at a size of 100-300 micrometer, for example. A 100-300 micron pixel size may be convenient to use, especially when the size of pathology searched for is of the same approximate size. However, in order to achieve a high resolution, a high frequency of spatial sampling should be used, for collecting overlapping illumination data, which may then be processed to create overlapping images of the pathology.

Figure 3:
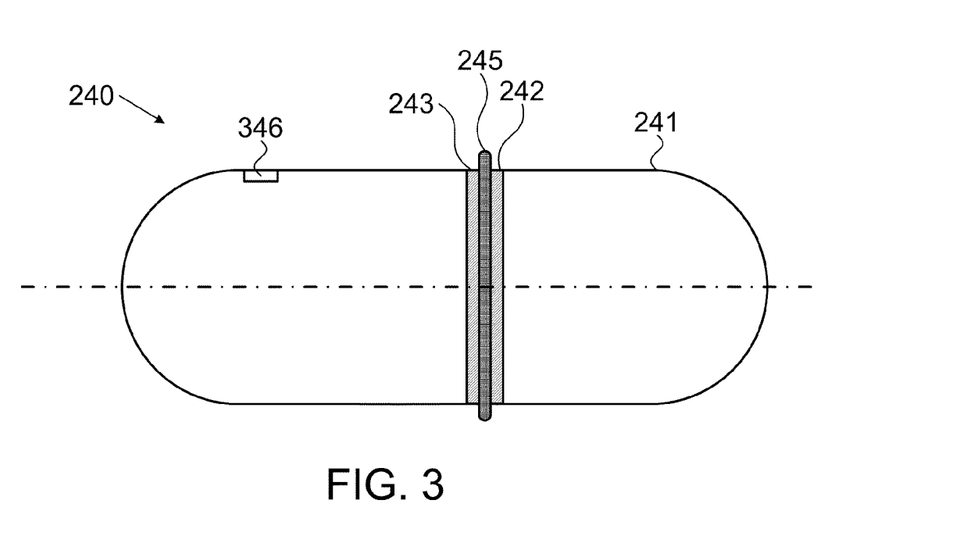
FIG. 3 is a schematic illustration of an in-vivo imaging device according to an embodiment of the invention.

Reference is now made to FIG. 3 which schematically illustrates an in vivo imaging device according to one embodiment of the invention. FIG. 3 illustrates another embodiment of device 240 as shown in FIG. 2, comprising a ring of illumination sources circling housing 241 of device 240. Device 240, which is typically capsule shaped, may further comprise a ring of light sensors 243 encircling housing 241. According to some embodiments, device 240 may have a surface profile other than a circular profile, e.g., an elliptical profile, and when so, the illumination sources and light sensors may surround the housing 241 in the same shape as device 240's profile, e.g., there may be an elliptical ring of illumination sources and light sensors surrounding housing 241. In yet other embodiments, the illumination sources and light sensors may have a shape of a half of a circle or half of a ring circling one of the convex ends of the housing 241, parallel to the longitudinal axis of housing 241.

According to some embodiments, illuminating body 242 may produce pixel sized illumination, by illuminating through pixel sized openings 2242. In other embodiments, illuminating body 242 may produce pixel sized illumination by illuminating with pixel sized illumination sources. In some embodiments, the optical windows may be designed such that they maintain high resolution of illumination, i.e., each optical window may comprise a narrow opening. According to some embodiments, light sensor(s) 243 may comprise a ring of pixel sized light sensors. In some embodiments, there may be more than one ring of light sensors 243 to collect light emitted or scattered from the lumen wall with which device 240 is in contact.

According to some embodiments of the present invention, the plurality of illumination sources 242 and plurality of light sensors 243, both of which may be positioned along the circumference of device 240, enable performing multiple scattering measurements on adjacent areas of the same tissue, substantially simultaneously. According to some embodiments, in each measurement the spatial and spectral distributions of the scattering may be measured substantially simultaneously.

According to some embodiments, there may be an additional sensor 346 on the same side of device 240 contacting the lumen, which sensor 346 may act as a tracking sensor. Sensor 346 may give an indication that the distance device 240 has passed along the GI tract. Sensor 346 may work in the same manner as a desktop computer "optical mouse" works. Sensor 346 may be similar to motion illumination detectors 23 and 24, as illustrated in FIG. 2A of U.S. Patent Application Publication No. 2008/0027329, entitled "SYSTEM, APPARATUS AND METHOD FOR MEASUREMENT OF MOTION PARAMETERS OF AN IN-VIVO DEVICE" of the common assignee of the present invention, which is incorporated herein by reference.

According to some embodiments, a bather or partition 245 is provided between illuminating body 242 ring and light sensors 243 ring(s). Bather 245 may prevent light from reflecting directly from illuminating body 242 onto light sensors 243, before penetrating the lumen wall, or may decrease the amount of such direct reflection. Bather 245 may be a torus or half a torus circling housing 241 or may have any other shape suitable for preventing direct light from reaching light sensors 243 before passing through the GI tract's tissue. Other partitions are possible; for example, according to some embodiments, the illuminating body's ring 242 and light sensors' ring 243 may be positioned in a niches or recessed parts of the housing 241, thereby being partitioned from one another so as not to allow direct light from illuminating body 242 to reach light sensor(s) 243 and/or decrease direct surface reflections.

Figure 4:
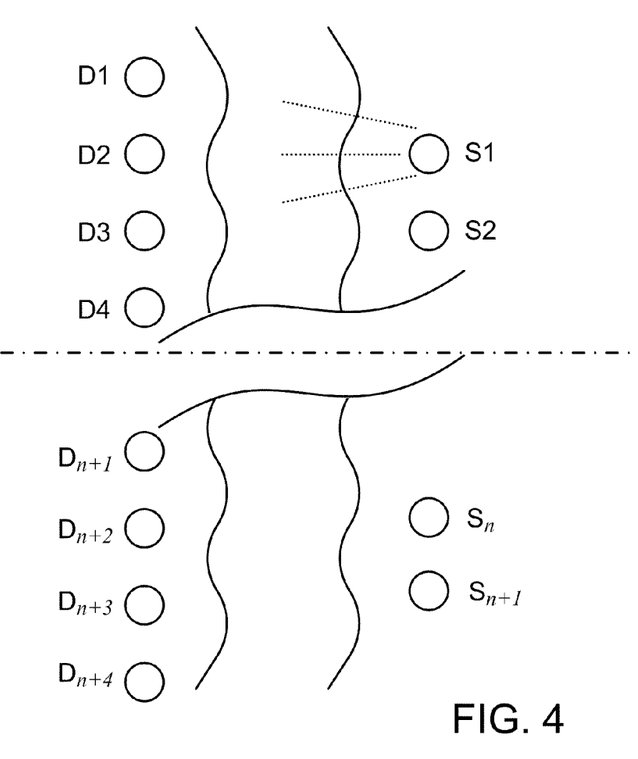
FIG. 4 is a schematic illustration of a section of an in-vivo imaging device according to an embodiment of the invention.

Reference is now made to FIG. 4, which is a schematic illustration of a section of an in-vivo imaging device according to an embodiment of the invention. According to some embodiments, device 240 may comprise pixel sized illumination produced by illuminating body 242 and pixel sized light sensors 243, as shown in FIG. 3, encircling housing 241 in a ring form or in other forms correlating to the shape of housing 241. Light source S1, which is part of illuminating body ring 242, may illuminate the lumen proximate to it. Then, detectors D1, D2 and D3, which are part of light sensors' ring 243, may detect or sense light which penetrate the tissue and is then emitted, scattered and/or remitted or emitted by fluorescence from the lumen tissue. Detectors D1, D2 and D3 may further detect scattered, remitted and/or light emitted by fluorescence from the lumen tissue following tissue penetration. Light source S2, which is also part of illuminating body ring 242, may illuminate the lumen, and light emitted from the lumen may be detected by detectors D2, D3 and D4, which are part of light sensors' ring 243. Detectors D2, D3 and D4 may sense light emitted by fluorescence, scattered and/or remitted from the lumen tissue following tissue penetration. The detectors may detect any kind of light emitted from the lumen tissue following tissue penetration. As different tissue structures have different scattering properties, the relative light intensity received by detectors D1, D2 and D3 may differ for different tissues, e.g., between normal tissue and carcinoma or between fatty tissue and muscles.

According to some embodiments, when light sources are positioned far enough from one another, such that photons from one pixel sized area of the lumen do not reach another pixel sized area of the lumen, then all of illuminating bodies 242 may be activated at once. This way, images from all around device 240 may be acquired at once, all providing information on the tissue and pathologies present in it.

In addition, a high frequency of sampling with detectors D1-Dn, for example of 10 samplings per second, will result in a high spatial resolution of the device perpendicularly to the forward motion of the device. On the lateral axis of device 240, which is the axis perpendicular to the forward motion of device 240 in the GI tract, when each illuminating body 242 is pixel sized of 100-300 micron, then a ring of light sources would contain around 350-400 pixels in a standard swallowable capsule with a diameter of around 11 mm. Therefore, resolution on the lateral axis is sufficient. However, on the longitudinal axis, in order to acquire the same approximate pixel size, the sampling frequency should be around 10 Hertz, and the flashing frequency of illuminating body 242 may only be around tenths of Hertz. For example, when light source S1 is illuminating, light is measured by detectors D1, D3 etc. And when light source S2 is illuminating, light is measured by detectors D2, D4, etc. This way, "sub-pixel" resolution is provided by analyzing the outputs of the detectors, which is somewhat deconvolution. Since the device 240 travels relatively slowly, flashing the diodes sequentially at 10 Hz is sufficient for getting the high resolution.

Figure 5:
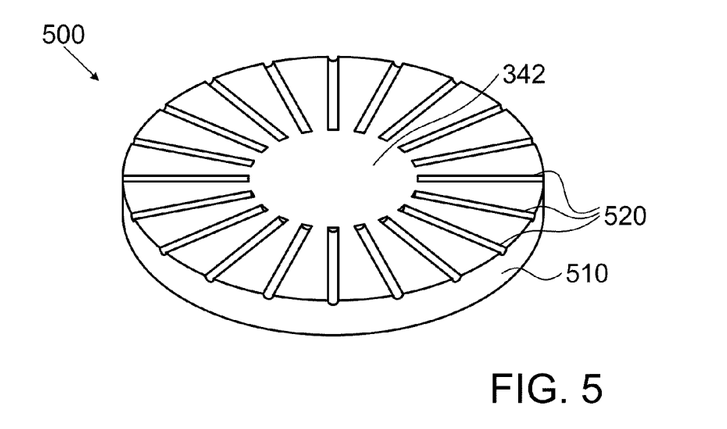
FIG. 5 is a schematic illustration of an illuminating body according to an embodiment of the invention.

Reference is now made to FIG. 5, which schematically illustrates a low cost method to produce an illuminating body or a sensing body according to an embodiment of the present invention. The illuminating or sensing bodies as described in FIG. 5 may be the same as illuminating and sensing bodies used in device 240 as shown in FIGS. 2, 3 and 4. In other embodiments, the illumination and sensing bodies may have the shape of a half of a circle or half of a ring, encircling one of the convex ends of the housing 241, parallel to the longitudinal axis of housing 241.

According to embodiments of the present invention both the array of light sensors and the array of illumination sources may be in the form of rings applied on dielectric material like plastic or a ring made of glass using processes generally used in the MEMS or micro electronics industry, thus maintaining a considerably low manufacturing cost. For example, the light sensors or a die level (unpacked) illumination source may be placed on a Printed Circuit Board (PCB). A transparent dielectric material like transparent plastic or glass may be placed on the PCB in order to conduct the light in a radial direction. A second non transparent cover may be placed in order to prevent light progression in an undesired non-radial direction.

Light penetration into the tissue is dependent on the illuminated wavelength. Short wavelengths, such as wavelengths from the blue spectra, may be scattered after penetrating to a superficial tissue layer that is close to the tissue surface. Longer wavelengths, such as wavelengths from the red or near infrared spectra, may penetrate deeper into the tissue. In some embodiments, spectral information may be used to estimate the severity of a lesion.

According to other embodiments of the present invention, the array of light sources may be composed of light sources illuminating at different wavelengths. The corresponding light sensors either may comprise suitable filters or may not. Such a low cost device, which is capable of spectral analysis, may also be produced by using processes generally used in the MEMS or micro electronics industry. In some embodiments, the light sensors may be coated with spectral filters. In other embodiments, the light sensors may not be coated with such spectral filters. In some embodiments, a variety of illumination sources each illuminating at a different narrow band wavelength may be placed on a PCB, and may be covered by a ring shaped opaque dielectric material like opaque plastic or black glass in order to prevent each of the illumination sources from illuminating in all directions. Tunnels or channels may be created along the circumference of the opaque ring, followed by electrical wiring connections to be made by lithography or any other method known in the art of semiconductors or MEMS wafer industry, such that light from each of the different illumination sources may be guided through a different tunnel or channel. Those rings can then be equipped with either light sensors or illumination sources of different wavelengths. When a pair of such rings is attached to one another, thereby creating a ring of light sensors alongside a ring of illumination sources, light may be emitted from the illumination sources in a ring shaped illumination, illuminating the tissue surrounding the circumference of the device without spectral cross-illumination, and the light sensors may detect light emitted from varying inner layers of the tissue that surround the circumference of the device.

The diameter of disc 500 may be the same as that of device 240, or may be smaller than it. According to other embodiments, device 240 need not be of a circular shape and may have other geometrical shapes. Accordingly, disc 500 may be of the same shape and area size as device 240, or may be of the same shape as but a smaller area than device 240. When adding a barrier 245 between light sources 242 and light sensors 243, the disc 500 diameter should be around the same or less than the diameter of device 240. When providing a partition between the light sources 242 and light sensors 243, and/or by having those light sources 242 and light sensors 243 recessed within housing 241, then the diameter of disc 500 should be less than that of device 240.

According to yet another embodiment, illumination source 342 may be placed on the center of illumination disc 500. On the surface of disc 500 there may be a construction of optical wave guides 520. Optical wave guides 520 may be in the form of channels for guiding the light from illumination source 342 therethrough and into pinpoint exits in order to achieve pinpoint illumination sources, e.g., pixel sized illumination sources. Wave guides 520 may be covered with a reflective material, e.g., aluminum, or any other material with the similar property of light reflection. At about the center of disc 500 at least one light source is provided whose illumination is guided through wave guides 520. At the outer end of each wave guide 520, which is at the periphery surface 510 of disc 500, are the pixel sized exits of light emitting sources 242. According to some embodiments, a window shaped as a ring and made of transparent biocompatible material, e.g., polycarbonate, may be covering or surrounding periphery surface 510 so as to distance periphery surface 510 of illumination disc 500 from the lumen wall. The window's width may be very small but it may be useful in preserving and keeping periphery surface 510 and the exits of illumination sources 242 intact.

This configuration of illuminating body disc 500 enables illumination on the lateral axis of device 240, which is typically the direction in which device 240 has contact with a lumen wall. Also, this configuration allows a distance between each pixel sized light source, so all light sources 242 on the disc or ring may be activated simultaneously, which is time multiplexing of light sources 242.

Figure 6:
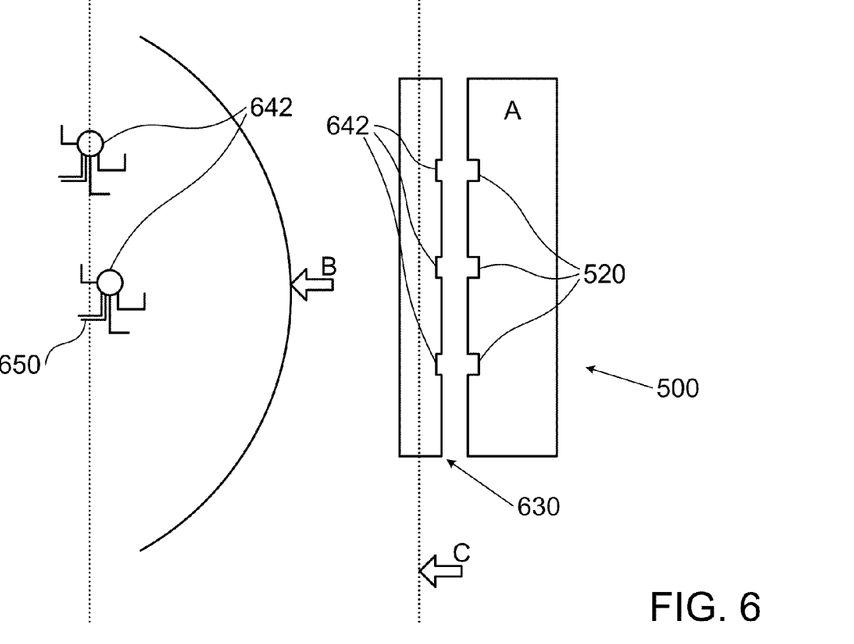
FIG. 6 is a schematic illustration of an illuminating body according to another embodiment of the present invention.

Reference is now made to FIG. 6, which schematically illustrates an illuminating body according to another embodiment of the present invention. According to an embodiment of the present invention, behind illumination disc 500 there may be a chip 630 (both illustrated in a side view) on which at least one illumination source 642 and its correlating electrical conductor/contact 650 are positioned. In other embodiments, the at least one illumination source 642 and electrical contact 650 may be embedded on chip 630. Chip 630 may be manufactured from silicon, gallium arsenide or any other semiconducting material known in the art for the manufacture of electrical chips.

Illumination disc 500 comprises wave guides 520, which are positioned so that illumination emitted from at least one illumination source 642 will pass into wave guides 520. According to some embodiments, wave guides 520 may be covered with a reflective material which assists in guiding the light through wave guides 520. Any reflective material may be used to cover the inner part of wave guide 520, for example, aluminum.

According to one embodiment, an upper view of chip 630 is also described, where electrical contacts 650 are on, or embedded in, chip 630. Illumination source(s) 642 are connected to electrical contacts 650 so that light may be emitted. Illumination source(s) 642 may comprise at least one diode or an array of diodes, e.g., an LED array. In other embodiments, illumination source(s) 642 may comprise a laser or an array of lasers, e.g., VCSEL lasers or diode lasers coupled with prisms. However, the number of illumination sources 642 may be lower than the number of pixel sized exits for illumination on the periphery of illumination disc 500, since wave guides 520 are guiding the illumination within towards the pixel sized exits on periphery 510 (as shown in FIG. 5).

According to some embodiments, as long as the pixel sized exits on periphery 510 of illumination disc 500 are far enough from each other, such that light from one pixel sized illumination source does not substantially intersect with light from another, then time multiplexing of illumination sources is possible and one diode or laser may activate several wave guides at once.

According to some embodiments, illumination sources 642, which may comprise a diode(s), a diode array, a laser or a laser array, may further comprise diode(s) or laser(s) which may illuminate in multiple wavelengths. In some embodiments, illumination sources 642 may comprise more than one wavelength of illumination such that wavelength multiplexing may take place. Illumination sources 642 may illuminate the lumen wall at one wavelength illuminated subsequent to a different wavelength, a process which is equivalent to wavelength multiplexing and may provide spectral information on the tissue, i.e., provide information on tissue characteristics. Each of the wavelengths illuminated may penetrate the lumen wall tissue and may then be scattered, be remitted or emit fluorescence from the lumen wall tissue. Such scattered and/or remitted or fluorescent light may indicate the color and texture of the tissue. A tissue's color and texture may provide information on different lumen wall characteristics, whether of normal tissue or abnormal tissue, e.g., pathologies.

In some embodiments, mainly but not limited to hyperspectral analysis, there may be a need for a more complex illumination disc which may comprise more than the two layers of illumination disc 500 and chip 630. There may be several layers and in between them passages for guiding light through wave guides and into pixel sized exits on periphery 510.

Figure 7:
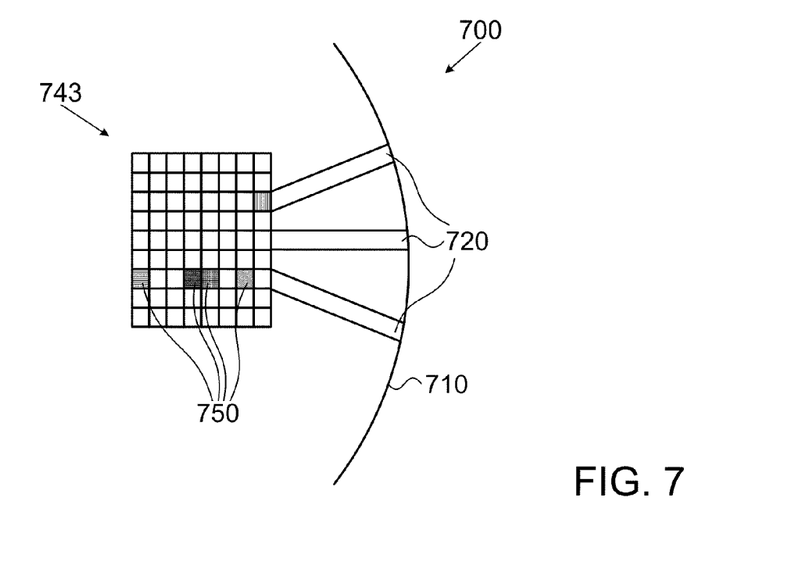
FIG. 7 is a schematic illustration of an array of light sensors according to an embodiment of the present invention.

Reference is now made to FIG. 7, which is a schematic illustration of an array of light sensors according to yet another embodiment of the present invention. According to some embodiments, there may be a light sensor disc 700 similar to illumination disc 500, which may be part of device 240. In some embodiments, there may be provided wave guides 720 which may guide light from outside device 240 and onto light sensor 743. According to some embodiments, each wave guide 720 may be coupled to a row, a column or a different setup of individual pixels on light sensor 743 pixel array. Therefore, light which penetrates the lumen wall and is then remitted by the lumen may be guided through wave guides 720 onto a row, a column or any other layout of pixels of light sensor 743.

According to some embodiments, light sensor 743 may comprise spectral filters 750 which may be placed on different pixels of each row, column or any other layout of light sensor 743. In some embodiments, filters 750 may be RGB filters. In other embodiments, filters 750 may be of other spectral regions/windows. The presence of various filters 750 on each row, column or other configuration of light sensor 743 may allow for light analysis in several spectral filters simultaneously such that device 700 may act as a spectral analysis device.

Figure 8:
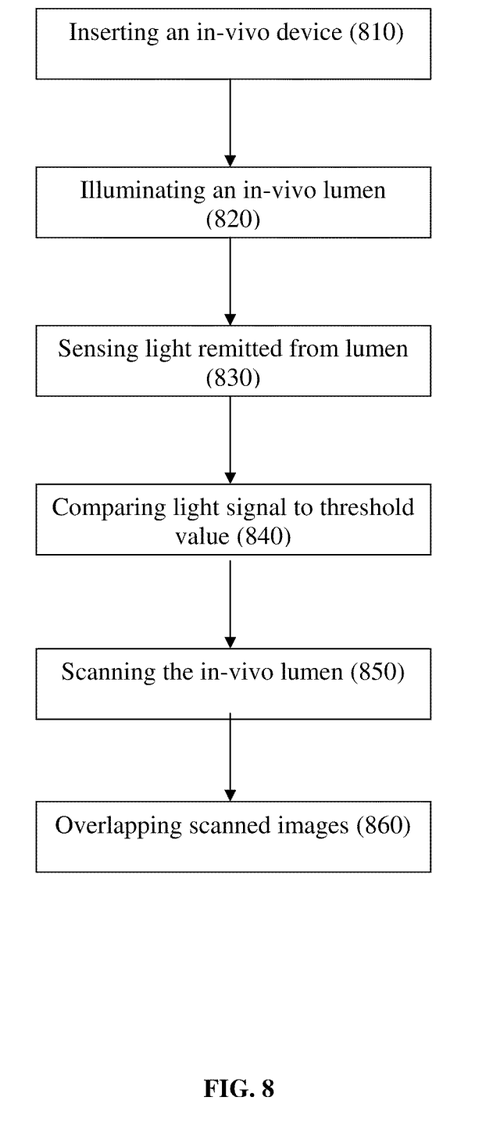
FIG. 8 depicts a method of optically scanning an in-vivo lumen tissue according to an embodiment of the present invention.

Reference is now made to FIG. 8, which depicts a method of optically scanning an in-vivo lumen tissue according to an embodiment of the present invention. According to some embodiments, in step 810 an in-vivo device is inserted into a patient's body, wherein the in-vivo device is typically a swallowable capsule, for example device 240. In other embodiments, the device may be inserted into the GI tract in other ways than swallowing, e.g., by surgery. In other embodiments, the in-vivo device may be part of an endoscope, e.g., part of the endoscope's tip, and as such may be inserted into a patient in the same way an endoscope is inserted into the body.

In step 820, the device, which may be device 240, may illuminate an in-vivo lumen at a constant or variable rate, e.g., 2-100 light excitations per second, and at the same time device 240 may measure the light intensity. When device 240 is not in contact with a lumen wall that is proximate to it, there may be reflected light that light sensor 243 may collect. The reflected light may cause light sensor 243 to be highly illuminated, thus producing a high signal.

When the device is in close proximity to or is substantially in contact with the lumen wall tissue, light may penetrate the lumen wall tissue and scatter prior to being reflected from the tissue and sensed by light sensors, which are part of the in-vivo device, e.g., light sensors 243. According to some embodiments, the illumination source may be pixel sized or there may be an illuminating body producing pixel sized illumination. In some embodiments, the illumination source may be illumination sources 242 or 642, as described in FIGS. 3 and 6, respectively.

According to some embodiments, in step 830, the light sensor in the in-vivo device senses light remitted from the lumen tissue after penetrating the lumen tissue and reflecting or scattering from it. The light sensor is positioned on the device so that direct light from the illumination source would not reach the light sensor, but would first penetrate through some of the lumen wall tissue. The light sensor may be pixel sized. According to some embodiments, the light sensor may be any of the light sensors 243 and 743 as described in FIGS. 3 and 7, respectively.

In step 840 the signal may be compared to a threshold value. If the light sensor is saturated or if the received light signal is above the threshold value, it may be inferred that the device 240 is not in close proximity to the lumen wall tissue. If the received light signal decreases continually even below threshold values, it may be inferred that the device 240 is moving farther away from the tissue. However, if the received light signal increases and then sharply decreases to values under the threshold value, it may be inferred that contact is achieved. Since scattered light is typically of a lower intensity than reflected light intensity, light signal value increasing correlates to the device receiving reflected light while getting closer to the tissue, whereas light signal value sharply decreasing thereafter correlates to the device being in contact with the tissue, thus scattered light is now collected and not reflected light.

In step 850, the lumen is being scanned by the in-vivo device, by continuously illuminating the lumen wall and sensing or detecting light remitted from the lumen, e.g., by repeating steps 820 to 840 during passage of the in-vivo device through the lumen. Scanning the lumen wall in such a way may provide spectral and spatial information on the lumen wall characteristics and of any pathology, if present. Additional data of deeper tissue condition may be collected if and when light penetrates into deeper layers of the tissue. In some embodiments, the device may be part of an endoscope, e.g., part of the endoscope's tip. Thus, scanning with an endoscope's tip or guided capsule may be done by moving the distal end of the endoscope's tip over the tissue, in a "push broom" sweeping motion, while keeping the endoscope's tip substantially in contact with the tissue.

According to some embodiments, markers indicating pathology may be inserted in-vivo (by swallowing, injecting, etc.) so that pathologies searched for may be selectively marked. Fluorescence may be emitted from the tissue and from in-vivo markers present in the tissue or in pathologies that have been selectively marked. In some embodiments, light absorption by the in-vivo markers compared to absorption by the lumen tissue surrounding the in-vivo markers may also indicate pathology.

In some embodiments, in step 860, information of emitted light that is scanned and collected by the light sensor may be overlapped in order to get a better resolution. In some embodiments, the overlapping light information may then be processed to create overlapping images of the pathology. The scanned light information that was overlapped may be further analyzed in order to collect the relevant information on tissue condition and of pathology present in the tissue. Other embodiments may take advantage of the fact that spectral analysis of scattered light may indicate pathologies located at a distance from the scanning point (deep into the tissue) such that a deeper portion of the GI tract may be scanned during one procedure. Due to the nature of spectral scattering, and due to the ring design of the illumination source and light sensor that enable collection of information all around the circumference of the device, large portions of the GI tract may be scanned at each location of the device, at any period of time. These embodiments may actually save the device's power and may enable a longer life time for the device.

It will be appreciated that the present invention is not limited to what has been particularly shown and described hereinabove. Rather the scope of the present invention is defined only by the claims which follow.

The invention claimed is:

1. An in-vivo sensing device for optically scanning an in-vivo lumen, comprising:
   an elongated housing having a cylindrical portion;
   at least one illuminating body providing illumination at the circumference of said cylindrical portion;
   at least one light sensor for sensing, at the circumference of said cylindrical portion, light that penetrated and was scattered from the tissue of said in vivo lumen; and a barrier located at the circumference of said cylindrical portion for decreasing the amount of direct light reflection from the surface of said in vivo lumen onto said at least one light sensor.

2. The device according to claim 1, wherein said illuminating body produces pixel sized illumination.

3. The device according to claim 2, wherein said pixel sized illumination is at the size of 300 microns at most.

4. The device according to claim 1, wherein said barrier is a torus or a half of a torus.

5. The device according to claim 1, wherein said at least one illuminating body and said at least one light sensor are illuminating and sensing, respectively, from a recessed position on said housing, and wherein the barrier is an area on the circumference of the housing between the at least one illuminating body and the at least one light sensor.

6. The device according to claim 1, wherein said illuminating body comprises a ring or half of a ring of wave-guides connecting between an illumination source and pixel sized optical openings surrounding the housing.

7. The device according to claim 1, wherein said light sensor comprises a ring or half of a ring of wave-guides connecting between a light sensor array and pixel sized optical openings surrounding the housing.

8. The device according to claim 6, wherein said light sensor comprises a ring or half of a ring of wave-guides connecting between said light sensor array and pixel sized optical openings surrounding the housing.

9. The device according to claim 6, wherein said illumination source is an LED or a laser.

10. The device according to claim 1, wherein said illuminating body comprises a plurality of narrow band wavelength illumination sources.

11. The device according to claim 10, wherein each of said plurality of narrow band wavelength illumination sources is an LED or a laser.

12. The device according to claim 7, wherein said light sensor array is a CMOS chip.

13. A method of optically scanning an in-vivo lumen tissue comprising the steps of:

(a) providing an in-vivo sensing device comprising:
   an elongated housing having a cylindrical portion;
   at least one illuminating body providing illumination at the circumference of said cylindrical portion;
   at least one light sensor for sensing, at the circumference of said cylindrical portion, light that penetrated and was scattered from the tissue of said in vivo lumen; and
   a barrier located at the circumference of said cylindrical portion, for decreasing the amount of direct light reflection from the surface of said in vivo lumen onto said at least one light sensor;

(b) illuminating an in-vivo lumen with said at least one illuminating body, so that light penetrates the lumen wall tissue and so that direct illumination from the at least one illuminating body is prevented from reaching the at least one light sensor;

(c) sensing light emitted from the lumen tissue onto said at least one light sensor; and (d) scanning the lumen by repeating steps (b) and (c) during passage of the in-vivo device through the lumen, (e) providing scanned light information.

14. The method according to claim 13, further comprising the step of analyzing the scanned light information for determining presence of pathology.

15. The method according to claim 13, further comprising the steps of:
   comparing the emitted light signal to a threshold value, wherein a value higher than the threshold correlates to said device being at a distance from the lumen tissue, and wherein a light signal value lower than the threshold correlates to the device moving farther away from the tissue, and wherein a light signal value increasing above threshold and then sharply decreasing below the threshold correlates to said device being in contact with the tissue.

16. The method according to claim 13, further comprising the step of overlapping the scanned light information in order to get better resolution.

* * * * *